(12) United States Patent
Matsui et al.

(10) Patent No.: US 6,291,718 B1
(45) Date of Patent: *Sep. 18, 2001

(54) PROCESS FOR PREPARING HYDROPEROXIDES

(75) Inventors: Shigekazu Matsui; Hiroshi Kuroda; Nobuya Hirokane; Haruyuki Makio; Toshihiro Takai; Koji Kato; Terunori Fujita; Makoto Kamimura, all of Yamaguchi-ken (JP)

(73) Assignee: Mitsui Chemicals, Inc., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/254,176

(22) PCT Filed: Jun. 30, 1998

(86) PCT No.: PCT/JP98/02935

§ 371 Date: Mar. 2, 1999

§ 102(e) Date: Mar. 2, 1999

(87) PCT Pub. No.: WO99/02491

PCT Pub. Date: Jan. 21, 1999

(30) Foreign Application Priority Data

Jul. 9, 1997 (JP) .................................................. 9-183291

(51) Int. Cl.⁷ ................................................ C07C 407/00
(52) U.S. Cl. ........................... 568/569; 568/571; 568/573
(58) Field of Search ................................... 568/561, 568, 568/569, 571, 573

(56) References Cited

U.S. PATENT DOCUMENTS

| 2,734,086 |   | 2/1956  | Goppel et al. . |         |
|-----------|---|---------|----------------|---------|
| 2,792,425 | * | 4/1957  | Weesner .      |         |
| 2,799,711 | * | 7/1957  | Beati .        |         |
| 2,951,799 | * | 9/1960  | Sharp .        |         |
| 3,160,668 | * | 12/1964 | Davie .        |         |
| 3,836,589 | * | 9/1974  | Angstadt .     |         |
| 4,299,991 | * | 11/1981 | Velenyi et al. | 568/573 |
| 4,602,118 | * | 7/1986  | Chou et al.    | 568/570 |
| 5,030,739 | * | 7/1991  | Foricher et al.| 552/542 |
| 5,395,980 | * | 3/1995  | Mueller        | 568/573 |

FOREIGN PATENT DOCUMENTS 48-49735  7/1973  (JP) .

OTHER PUBLICATIONS

J Am Chem Soc "Preparation and Reactions of Unsymmetrically Labeled Hydroperoxides: Solvent Viscosity Dependent Oxygen Scrambling of Cumylperoxyl Free Radicals" by Caldwell vol. 117 pp 8676, 1995.*
CA:71:101458 abs of Chem Stosow Ser A by Karminski, 13(2) pp 1751, 1969.*
CA:66:33408 abs of Mol Phys by Christiane, 11(3) pp 257–63, 1966.*
Berentsveig et al., *Bull. Acad. USSR. Div. Chem. Sci.*, vol. 31, No. 10, pp. 1949–1952 (1982).
Pryor et al., *J. Org. Chem.*, vol. 50, No. 2, pp. 185–189 (1985).

* cited by examiner

*Primary Examiner*—Jean F. Vollano
(74) *Attorney, Agent, or Firm*—Birch, Stewart, Kolasch & Birch, LLP

(57) ABSTRACT

A process for preparing hydroperoxides which comprises oxidizing hydrocarbon by a gas containing oxygen in the presence of a specific compound and converting them selectively to corresponding hydroperoxides. The specific compound is the compound that can capture radicals. The preferable example may be a compound selected from radicals of oxygen, nitrogen, phosphorus, sulfur, carbon or silicon or a compound that forms radicals of these in the reaction system. The present invention can be applied to oxidation of hydrocarbons including arylalkylhydrocarbons such as cumene, m-diisopropylbenzene, p-diisopropylbenzene, 1,3,5-triisopropylbenzene, isopropylnaphthalene, diisopropylnaphthalene, isopropylbiphenyl, diisopropylbiphenyl, etc.

24 Claims, No Drawings

PROCESS FOR PREPARING HYDROPEROXIDES

This application is the national phase under 35 U.S.C. §371 of prior PCT International Application No. PCT/JP98/02935, now WO99/02491, which has an International filing date of Jun. 30, 1998 which designated the United States of America.

TECHNICAL FIELD

The present invention relates to a process for preparing hydroperoxides, which comprises oxidizing hydrocarbon by a gas containing oxygen and converting it selectively to corresponding hydroperoxides.

TECHNICAL BACKGROUND

The process of oxidizing hydrocarbon by a gas containing oxygen in the absence of a catalyst to prepare corresponding hydroperoxides is known as autoxidation technology. However, in this reaction, it is necessary to raise the reaction temperature to increase the rate of accumulation of hydroperoxides. Nevertheless, when the reaction temperature is raised to increase the rate of accumulation, the reaction product hydroperoxide is thermally decomposed, resulting in a decline in its selectivity. In other words, since there was such relationship between the rate of accumulation and selectivity that as either one goes up, the other goes down, it was difficult to maintain both of them at high levels.

Attempts have been made to oxidize hydrocarbon in the state of gas containing oxygen by a catalyst to produce an effect on the rate of accumulation and/or selectivity in producing corresponding hydroperoxides (Japanese Patent Publication SHO 55-50020, for example).

The inventors of the present invention firmly believed that there should be a way to achieve high selectivity, while overcoming the relationship between the rate of accumulation and selectivity and maintaining a commercially viable rate of accumulation at the same time. With this belief, the inventors continued research assiduously. As a result, the inventors successfully made an invention to solve the problem.

In the course to the invention, inventors found that a oxidation of a hydrocarbon by a gas containing oxygen in the presence of a specific compound is effective for converting it to the corresponding hydroperoxides.

Specifically, the present invention provides a method for oxidizing hydrocarbon by a gas containing oxygen thereby to prepare corresponding hydroperoxides at a high selectivity.

DISCLOSURE OF THE INVENTION

The process for preparing hydroperoxides by the present invention is based on the attainment of a very high selectivity possible by the use of a compound capable of capturing radicals as a specified compound in the process of oxidizing hydrocarbon by a gas containing oxygen. The present invention is characterized by oxidizing hydrocarbon by a gas containing oxygen in the presence of a compound that can capture radicals and converting it selectively to corresponding hydroperoxides.

THE BEST MODE EMBODIMENT OF THE INVENTION

Examples of the starting material hydrocarbon include paraffin having secondary carbon, olefin, cycloparaffin and arylalkyl hydrocarbon. Specific preferable examples of the starting material include, but are not limited to, isobutene, etc. as paraffin having secondary carbon; pentene, isobutene, etc. as olefin; cyclopentane, cyclohexane, etc. as cycloparaffin; and cumene, cymene, etc. as arylalkyl hydrocarbon.

The compound represented by the following general formula (I) may be cited as an example of the arylalkyl hydrocarbon: Compound of the general formula (I):

(wherein P and Q stand for hydrogen or the alkyl group, which may be the same or different from each other; t stands for a whole number of 1 to 3; and Ar stands for the aromatic hydrocarbon group of the t value.)

In the general formula (I), it is preferable that at least either of P and Q is the alkyl group, especially preferable that both of them are alkyl groups. Especially the methyl group is preferable as the aforementioned alkyl group. Further, a hydrocarbon group having the t value that can be derived from benzene, naphthalene, biphenyl, diphenyl ether, etc., preferable a hydrocarbon group of the t value that is derived from benzene or naphthalene, may be cited as examples of the aromatic hydrocarbon group.

Therefore, in the present invention, preferable examples of the arylalkyl hydrocarbon include,but not limited to, diisopropylbenzenes such as cumene, cymene, m-diisopropylbenzene and p-di-isopropyl benzene, triisopropylbenzenes such as 1,3,5-tri-isopropylbenzene, ethylbenzene, sec-butylbenzene, sec-butylethylbenzene, isopropylnaphthalenes, diisopropylnaphthalene such as 2,6-diisopropyl naphthalene, isopropyl diphenyls, diisopropylbiphenyls such as 4,4'-diisopropylbiphenyl, and mixtures of not less than two of these. Cumene is most preferable.

The compound of the present invention that can capture radicals refers to a compound having the ability to capture radicals, and it does not matter whether the compound itself possesses such ability or such ability is given to the compound under reaction conditions.

Examples of the compound of the present invention that can capture radicals include radicals of oxygen, nitrogen, phosphorus, sulfur, carbon and silicon, and the compounds that form these radicals in the reaction system.

In the preparation of the present invention, either those radicals which are stable at room temperature or those compounds which form radicals under reaction conditions may be used.

In the reaction of oxidizing hydrocarbon by a gas containing oxygen, various by-products are formed. In the case of the example of the autoxidation of cumene, dimethylphenylcarbinol, acetophenone and dicumylperoxide may be cited as examples of such by-products. It is presumed that there are alkyl radicals such as cumyl radical and cumenehydroperoxy radical, hydroxy radical, etc. present in the process of reaction. It is presumed in the present invention that the compound that can capture radicals acts on these radicals in some respects, such as capturing the radicals inducing the reaction of the formation of such by-products, and consequently the selectivity of the hydroperoxide corresponding to the raw material hydrocarbon is improved.

In selecting the compound that can capture radicals in the present invention, it is possible to use the difference in the SOMO (single occupied molecular orbit) energy level (Δε (SOMO)) between the radical of or derived from said compound that can capture radicals, and the radicals to be captured. The SOMO energy level is calculated by the method as described below. It is desirable to select such compound capable of capturing radicals that the difference in the SOMO energy level, Δε(SOMO), is normally 0 to 10 eV, preferably 0 to 4 eV, more preferably 0 to 1 eV.

For example, it is desirable to select such compound capable of capturing radicals in the present invention that its relationship with the radical (formula I-2 below) corresponding to the hydrocarbon to be oxidized is as follows:

$$\Delta\epsilon(SOMO) = |\epsilon a(SOMO) - \epsilon b(SOMO)| = 0 \text{ to } 10 \text{ eV}$$

wherein ε a (SOMO) stands for the SOMO energy level of the compound cable of capturing radicals or the radical formed therefrom, and εb (SOMO) stands for the SOMO energy level of the radical corresponding to the hydrocarbon to be oxidized.

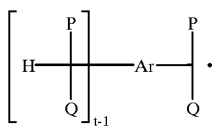

(I-2)

(wherein P and Q, standing for hydrogen or the alkyl group, may be the same or different from each other; t stands for a whole number of 1 to 3; and Ar stands for the aromatic hydrocarbon group of the t value.)

ε(SOMO) Calculation Method

The structural calculation of a radical is made by a semiempirical molecular orbit method (MNDO-PM3 method: MOPAC program) to calculate ε(SOMO).

The ε(SOMO) of those which are not a radical is determined by the structural calculation of the corresponding radical.

As the aforementioned Δε(SOMO) becomes lower, the hydrocarbon radical is easier to capture. The Δε(SOMO) is normally in the range of 0 to 10 eV, preferably 0 to 4 eV, more preferably 0 to 1 eV.

The use of a compound having a proper value of Δε(SOMO) has the characteristic that in comparison with the case of adding no such compound, the selectivity goes up over the selectivity of hydroperoxide in other reaction at the same rate of accumulation. Because of this, the use of such compound enables hydrocarbon to be converted at high selectivity and at a high concentration.

Oxygen radical and a compound that forms oxygen radical in the reaction system can be cited as one specific example of the compound that can capture radicals.

As the oxygen radical of the present invention, the compound represented by the general formula (II):

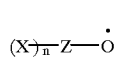

(II)

(wherein Z stands for nitrogen, sulfur or phosphorus; X stands for any substitutional group; and n stands for a whole number of 1 to 4 satisfying the value of Z) or a compound that forms the compound represented by the general formula (II) in the reaction system can be cited.

As the substitutional group X of the general formula (II), the following can be cited: X, which may be the same or different from each other, may be hydrogen atom, halogen atom, hydrocarbon group, heterocyclic compound residue, oxygen-containing group, nitrogen-containing group, boron-containing group, sulfur-containing group, phosphorus-containing group or silicon-containing group, or a ring formed by not less than two of these being connected to each other.

As halogen atom, fluorine, chlorine, bromine and iodine. Specific examples of the hydrocarbon group include straight-chain or branched alkyl groups having 1 to 30, preferably 1 to 20, carbon atoms, such as methyl, ethyl, n-propyl, isopropyl, n-butyl, isobutyl, sec-butyl, tert-butyl, neopentyl and n-hexyl; straight-chain or branched alkenyl groups having 2 to 30, preferably 2 to 20, carbon atoms, such as vinyl, aryl and isopropenyl; straight-chain or branched alkinyl group having 2 to 30, preferably 2 to 20 carbon atoms, such as ethynyl and propargyl; cyclic saturated hydrocarbon groups having 3 to 30, preferably 3 to 20, carbon atoms, such as cyclopropyl, cyclobutyl, cyclopentyl, cyclohexyl and adamantyl; cyclic unsaturated hydrocarbon group having 5 to 30 carbon atoms such as cyclopentadienyl, indenyl and fluorenye and aryl groups having 6 to 30, preferably 6 to 20, carbon atoms, such as phenyl, benzyl, naphthyl, biphenyl, terphenyl, phenanthryl and anthracenyl.

Hydrogen atom in the aforementioned hydrocarbon group may be substituted by halogen atom. Examples of such hydrocarbon group include halogenated hydrocarbon groups having 1 to 30, preferably 1 to 20, carbon atoms, such as trifluoromethyl, pentafluorophenyl and chlorophenyl.

Furthermore, the aforementioned hydrocarbon group may be substituted by other hydrocarbon groups mentioned above. Examples of such hydrocarbon group include aryl-group-substituted alkyl groups such as benzyl and cumyl; alkyl-group-substituted aryl groups such as tolyl, isopropylphenyl, t-butylphenyl, dimethylphenyl and di-t-butylphenyl; and substituted aryl groups in which an aryl group is substituted by alkoxy group, aryl group or aryloxy group. Moreover, the aforementioned hydrocarbon groups may contain the heterocyclic compound residue, oxygen-containing group, nitrogen-containing group, boric acid-containing group, sulfur-containing group, phosphorus-containing group or silicon-containing group mentioned below.

Out of them, especially preferable hydrocarbon groups are particularly straight-chain or branched alkyl groups having 1 to 30, preferably 1 to 20, carbon atoms, such as methyl, ethyl, n-propyl, isopropyl, n-butyl, isobutyl, sec-butyl, tert-butyl, neopentyl and n-hexyl; aryl groups having 6 to 30, preferably 6 to 20, carbon atoms, such as phenyl, naphthyl, biphenyl, terphenyl, phenanthryl and anthracenyl; and substituted aryl groups having 1 to 5 of substituents such as alkyl group or alkoxy group having 1 to 30, preferably 1 to 20 carbon atoms, and aryl group or aryloxy group having 6 to 30, preferably 6 to 20 carbon atoms.

Examples of the heterocyclic compound residue include residues of nitrogen-containing compounds such as pyrrole, pyridine, pyrimidine, quinoline and triazine; oxygen-containing compounds such as furan and pyrane; residues of sulfur-containing compounds such as thiophene; and groups having these heterocyclic compound residues further substituted by substitutional groups such as the alkyl group and alkoxy group having 1 to 30, preferably 1 to 20 carbon atoms.

Examples of the oxygen-containing group include the alkoxy group, aryloxy group, ester group, acyl group, carboxyl group, carbonate group, hydroxy group, peroxy group and carboxylic acid anhydride group.

Examples of the alkoxy group, out of these, include the alkoxy group having 1 to 30 carbon atoms, specifically, methoxy, ethoxy, n-propoxy, isopropoxy, n-butoxy, isobutoxy and tert-butoxy. Examples of the aryloxy group include the aryloxy group having 6 to 30 carbon atoms, specifically, phenoxy, 2,6-dimethylphenoxy and 2,4,6-trimethylphenoxy. Examples of the ester group include the ester group having 1 to 30 carbon atoms, specifically, acetyloxy, benzoyloxy, methoxycarbonyl, phenoxycarbonyl and p-chlorophenoxycarbonyl. Examples of the acyl group include the acyl group having 1 to 30 carbon atoms, specifically, the formyl group, acetyl group, benzoyl group, p-chlorobenzoyl group and p-methoxybenzoyl group.

Examples of the nitrogen-containing group include the amino group, imino group, amide group, imide group, hydrazino group, hydrazono group, nitro group, nitroso group, cyano group, isocyano group, ester cyanate group, amidino group, diazo group and amino group having turned into ammonium salt.

Examples of the amino group, out of these, include the amino group having 0 to 30 carbon atoms, specifically, dimethylamino, ethylmethylamino and diphenylamino. Examples of the imino group include the imino group having 1 to 30 carbon atoms, specifically, methylimino, ethylimino, propylimino, butylimino and phenylimino. Examples of the amido group include the amido group having 1 to 30 carbon atoms, specifically, acetoamido, N-methylacetoamido and N-methylbenzamino. Examples of the imido group is the imido group having 2 to 30 carbon atoms, specifically, acetoimido and benzimido.

Examples of the boron-containing group include the boranediye group, boranetolyl group and diboranyl group.

Examples of the sulfur-containing group include the mercapto group, thioester group, dithioester group, alkylthio group, arylthio group, thioacyl group, thioether group, thiocyanate group, isocyanate group, sulfonester group, sulfonamide group, thiocarboxyl group, dithiocarboxyl group, sulfo group, sulfonyl group, sulfinyl group and sulphenyl group.

Examples of the thioester group, out of these, include the thioester group having 1 to 30 carbon atoms, specifically, acetylthio, benzoylthio, methylthiocarbonyl and phenylthiocarbonyl. Examples of the alkylthio group include the alkylthio group having 1 to 30 carbon atoms, specifically, methylthio and ethylthio. Examples of the sulfonamide group include the sulfonamide group having 0 to 30 carbon atoms, specifically, phenylsulfonamide, N-methylsulfonamide and N-methyl-p-toluene-sulfonamide. Examples of the arylthio group include the arylthio group having 6 to 30 carbon atoms, specifically, phenylthio, methylphenylthio and naphthylthio. Examples of the sulfonester group include the sulfonester group having 1 to 30 carbon atoms, specifically, methyl sulfonic acid, ethyl sulfonic acid and phenyl solfonic acid.

Examples of the phosphorus-containing group include the phosphide group, phosphoryl group, thiophosphoryl and phosphato group.

Examples of the silicon-containing group include the silyl group, siloxy group, hydrocarbon-substituted silyl group, hydrocarbon-substituted siloxy group, specifically, methyl silyl, dimethylsilyl, trimethylsilyl, ethylsilyl, diethylsilyl, triethylsilyl, diphenylmethylsilyl, triphenylsilyl, dimethylphenylsilyl, dimethyl-t-butylsilyl, and dimethyl (pentafluorophenyl)silyl. Out of these, methyl silyl, dimethylsilyl, trimethylsilyl, ethylsilyl, diethylsilyl, triethylsilyl, dimethylphenylsilyl and triphenylsilyl are preferable. Especially, trimethylsilyl, triethylsilyl, triphenylsilyl and dimethylphenylsilyl are preferable. Specific examples of the hydrocarbon-substituted siloxy group include trimethylsiloxy.

Examples of the general formula (II) include, but are not limited to, the following, for example:

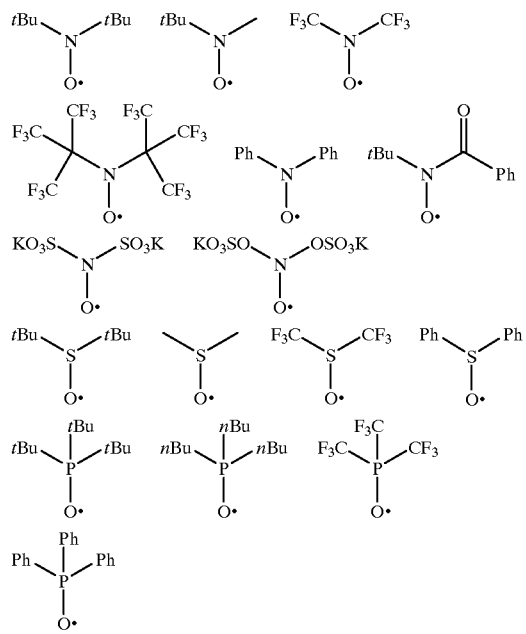

In the general formula (II), a compound represented by the following general formula (III) may be cited as an example of nitroxide radical.

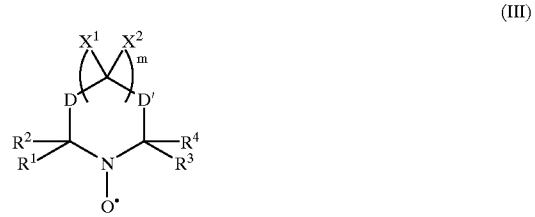

(III)

(wherein m stands for a whole number of 0 to 3; and -D- and -D'- stand each separately for:

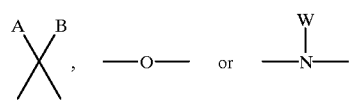

A, B, $X^1$, $X^2$, $R^1$, $R^2$, $R^3$, $R^4$ and W stand each separately for hydrogen or a substitutional group comprising an element selected from among hydrogen, carbon, oxygen, nitrogen, sulfur, Phosphorus, silicon and halogen; and each ring member carbon atom or each ring member nitrogen atom may form a double bond between adjoining atoms).

The substitutional group in the general formula (III) may be the same group as cited as an example of the substitutional group X in the aforementioned general formula (II). Preferable examples of the hydrogen or the substitutional groups of the general formula (III) are hydrogen, alkyl group, aryl group, halogen, cyano group, amino group, isothiocyanic acid group, —COORa (wherein Ra stands for hydrogen, alkyl group and aryl group), (di)alkylaminoalkyl group, hydroxyl group, hydroxyalkyl group, alkoxy group, arylalkoxy group, —CONRbRc (wherein Rb and Rc are each separately hydrogen. alkyl group and aryl group), oxo group (=O), maleimide group, phosphoric acid group, =NH group or bivalent group.

The examples of the aforementioned nitroxide radicals may include a compound having a structure in which two or more structures of the general formula (III) are crosslinked through any of the groups of $X^1$, $X^2$, A, B and W.

In the general formula (III), it is preferable that all of R1, R2, R3 and R4 are groups selected from alkyl groups. For example, 2,2,6,6-teraalkylpiperidinoxy radical, 4-hydroxy-2,2,6,6-tetraalkyl piperidinyloxy radical, bis-(2,2,6,6-teraalkyl piperidinoxyl)-sebacate or 2,2,5,5-teraalkyl pyrrolidinoxy radical or the said compound substituted by the aforementioned group may be cited as preferable compounds.

Specific examples of the compound of the general formula (III) include, but are not limited to, the following:

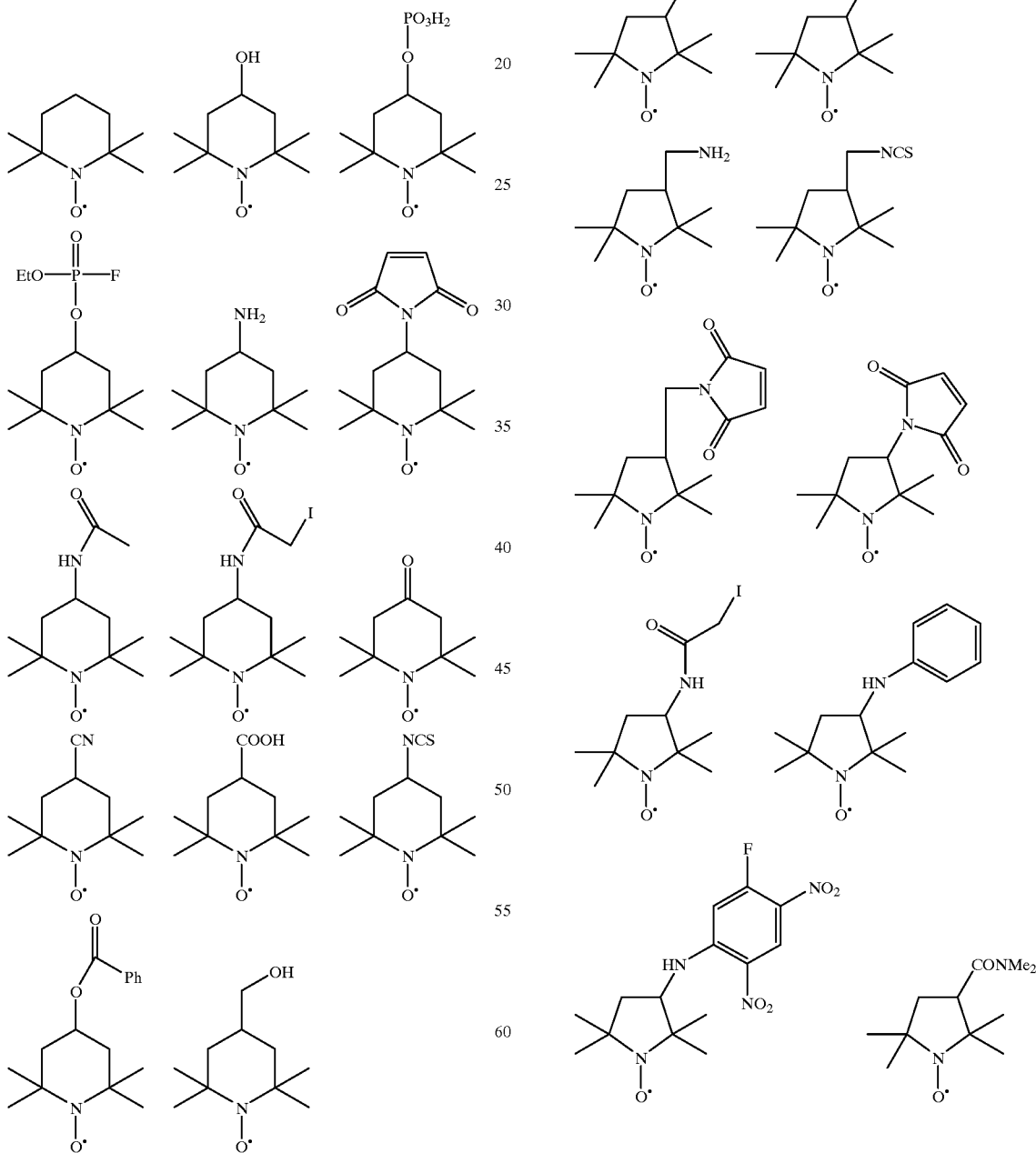

-continued

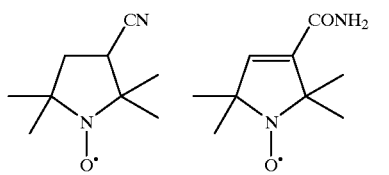

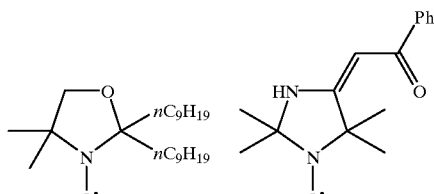

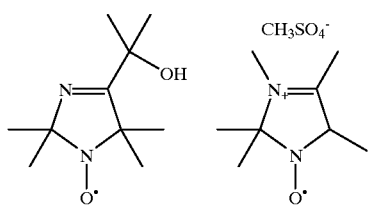

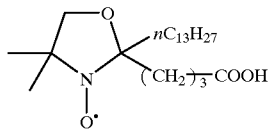

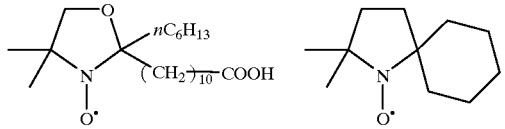

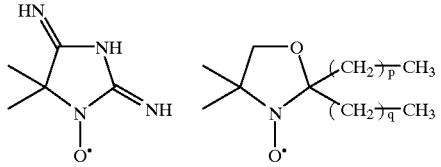

(wherein Me stands for the methyl group; Et stands for the ethyl group; and Ph stands for the phenyl group: This hereinafter applies to the present invention. Further, p and q stand for a whole number Of 0 to 30, respectively.)

As the compound that turns into nitroxide radical under reaction conditions, the compound that turns into nitroxide radical represented by the aforementioned general formula (III) under reaction conditions or the compounds represented by the following general formulas (V), (VI) and (VII).

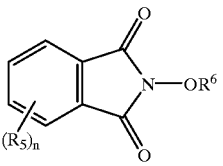

(V)

(wherein n stands for a whole number of 0 to 4; and $R_5$ and $R^6$ stand each separately for hydrogen or a substitutional group comprising an element selected from among hydrogen, carbon, oxygen, nitrogen, sulfur, phosphorus, silicon and halogen.)

Each of the substitutional groups in the general formula (V) may be the same group as cited as an example of the substitutional group X in the aforementioned general formula (II). A preferable example of $R_5$ may be halogen, alkyl group, arylalkyl group, alkoxy group or arylalkoxy group, and a preferable example of R6 may be hydrogen or the alkyl group.

As examples of each of substitutional groups of the general formula (V), halogen includes F, Cl, Br and I; the alkyl group preferably includes the alkyl group having 1 to 10 carbon atoms, such as the methyl group, ethyl group, n-propyl group, i-propyl group, n-butyl group, i-butyl group, sec-butyl group, t-butyl group and isoamyl group; the arylalkyl group includes cumyl group ; the alkoxy group preferably includes the alkoxy group having 1 to 10 carbon atoms, such as methoxy group, ethoxy group, n-propoxy group, i-propoxy group, n-butoxy group, i-butoxy group, sec-butoxy group and t-butoxy group; and the arylalkoxy group includes cumyloxy group.

Specific examples of the compound of the general formula (V) include, but are not limited to, N-hydroxyphthalimide and N-methoxyphthalimide:

(VI)

(wherein $R^7$, $R^8$ and $R^9$ stand each separately for hydrogen or a substitutional group comprising an element selected from among hydrogen, carbon, oxygen, nitrogen, sulfur, phosphorus, silicon and halogen.)

Each of the substitutional groups in the general formula (VI) may be the same group as cited as an example of the substitutional group X in the aforementioned general formula (II). Preferable examples of the substitutional groups are halogen, alkyl group, or haloalkyl group for $R^7$, $R^8$ and $R^9$.

As examples of each of substitutional groups of the general formula (VI), halogen includes F, Cl, Br and I; the alkyl group preferably includes the alkyl group having 1 to 10 carbon atoms, such as the methyl group, ethyl group, n-propyl group, i-propyl group, n-butyl group, i-butyl group, sec-butyl group, t-butyl group and isoamyl group; and the haloalkyl group includes trifluoromethyl group.

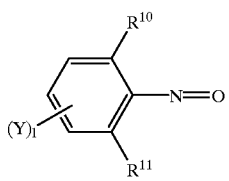

(VII)

(wherein l stands for a whole number of 0 to 3; and Y, $R^{10}$ and $R^{11}$ stand each separately for hydrogen or a substitutional group comprising an element selected from among hydrogen, carbon, oxygen, nitrogen, sulfur, phosphorus, silicon and halogen.)

Each of the substitutional groups in the general formula (VII) may be the same group as cited as an example of the substitutional group X in the aforementioned general formula (II). Preferable examples of the substitutional groups are halogen, alkyl group, arylalkyl group, alkoxy group or arylalkoxy group.

Halogen includes F, Cl, Br and I; the alkyl group preferably includes the alkyl group having 1 to 30 carbon atoms, such as the methyl group, ethyl group, n-propyl group, i-propyl group, n-butyl group, i-butyl group, sec-butyl group, t-butyl group and isoamyl group; the arylalkyl group includes cumyl group; the alkoxy group preferably includes the alkoxy group having 1 to 30 carbon atoms, such as methoxy group, ethoxy group, n-propoxy group, i-propoxy group, n-butoxy group, i-butoxy group, sec-butoxy group and t-butoxy group; and the arylalkoxy group includes cumyloxy group.

Specific examples of the compound that can capture radicals include a nitrogen radical or a compound that forms a nitrogen radical in the reaction system.

Specific examples of the compound that can capture these radicals include, but are not limited to, the following:

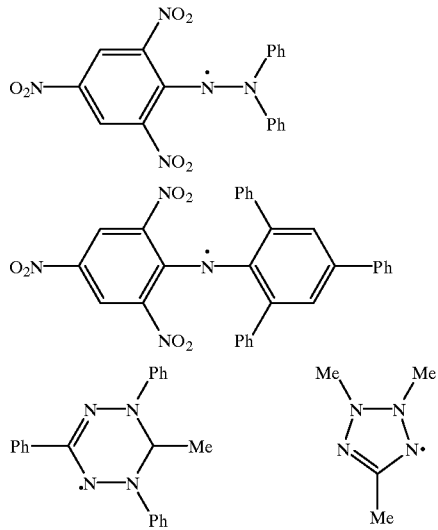

Specific examples of the compound that can capture radicals include a phosphorous radical or a compound that forms a phosphorus radical in the reaction system.

Specific examples of the compound that can capture these radicals include, but are not limited to, the following:

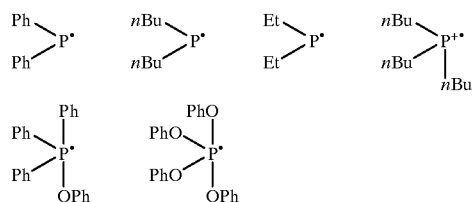

Specific examples of the compound that can capture radicals include a sulfur radical or a compound that forms a sulfur radical in the reaction system.

Specific examples of the sulfur radical include, but are not limited to, the following:

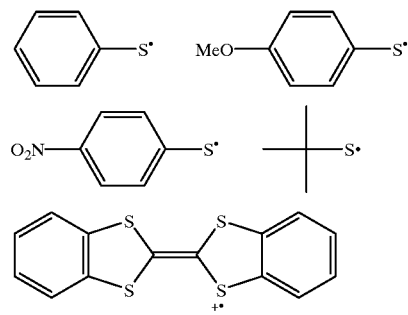

Specific examples of the compound that can capture radicals include a carbon radical or a compound that forms a carbon radical in the reaction system.

Specific examples of the carbon radical include, but are not limited to, the following:

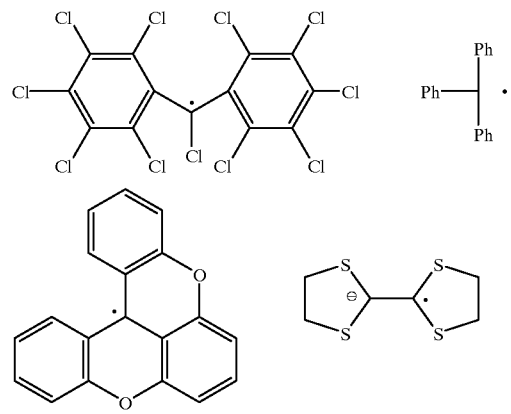

Specific examples of the compound that can capture radicals include a silicon radical or a compound that forms a silicon radical in the reaction system.

Specific examples of the silicon radical include, but are not limited to, the following:

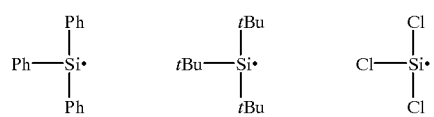

The compound that can capture radicals include secondary amine. Preferably the secondary amine represented by the following general formula (IV) may be cited.

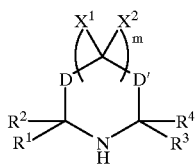

(IV)

(wherein m stands for a whole number of 0 to 3; -D- and -D'- stand each separately:

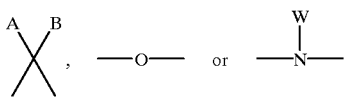

A, B, $X^1$, $X^2$, $R^1$, $R^2$, $R^3$, $R^4$ and W stand each separately for hydrogen or a to substitutional group comprising an element selected from among hydrogen, carbon, oxygen, nitrogen, sulfur, phophorus, silicon and halogen; and each ring member carbon atom or each ring member nitrogen atom may form a double bond between adjoining atoms).

The substitutional group in the general formula (IV) may be the same group as cited as an example of the substitutional group X in the aforementioned general formula (II). Preferable examples of the hydrogen or other substitutional groups of the general formula (IV) are hydrogen, alkyl group, aryl group, halogen, cyano group, amino group, isothiocyanic acid group, —COORa (wherein Ra stands for hydrogen, alkyl group and aryl group), (di)alkylaminoalkyl group, hydroxyl group, hydroxyalkyl group, alkoxy group, arylalkoxy group, —CONRbRc (wherein Rb and Rc are each separately hydrogen, alkyl group and aryl group), oxo group (=O), maleimide group, phosphoric acid group, =NH group or bivalent group.

The substitutional groups, which may be the same or different from each other, may be hydrogen atom, halogen atom, hydrocarbon group, heterocyclic compound residue, oxygen-containing group, nitrogen-containing group, boron-containing group, sulfur-containing group, phosphorus-containing group or silicon-containing group, or a ring formed by not less than two of these being connected to each other.

The examples of the aforementioned secondary amine may include a compound having a structure in which two or more structures of the general formula (IV) are crosslinked through any of the radicals of $X^1$, $X^2$, A, B and W.

In the general formula (IV), the preferable compounds are that all of $R^1$, $R^2$, $R^3$ and $R^4$ are groups selected from the alkyl group. For example, they include 2,2,6,6-tetraalkyl piperidine, 2,2,6,6-tetraalkyl-4-piperidinol, bis-(2,2,6,6-tetraalkyl piperidinyl)-sebacate or 2,2,5,5-tetraalkyl pyrrolidine, or the said compound substituted by the aforementioned group.

Specific examples of the secondary amine include, but are not limited to, the following:

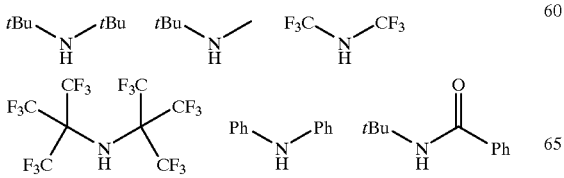

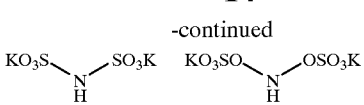

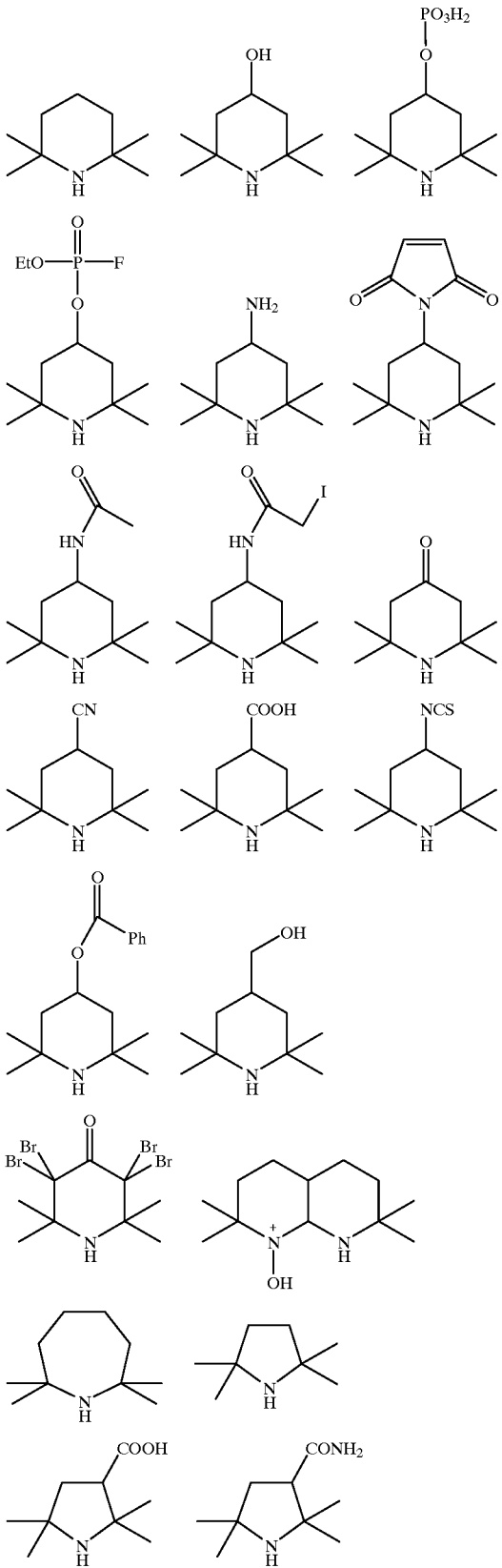

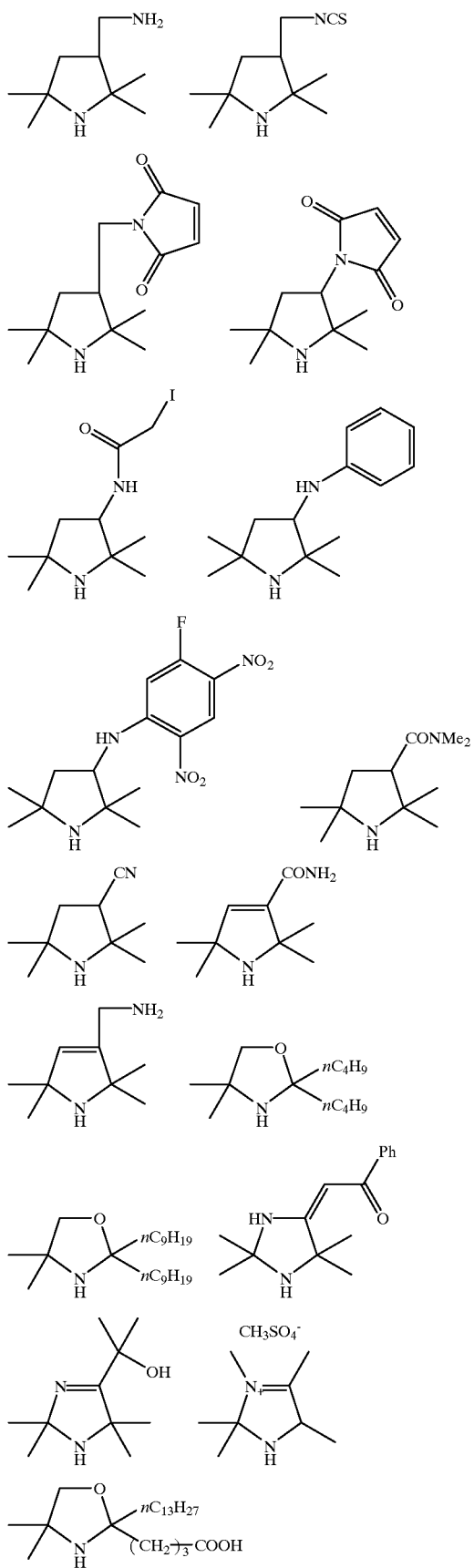
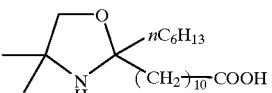

For the compound that can capture radicals, hindered phenols represented by the general formula (VIII) may be cited.

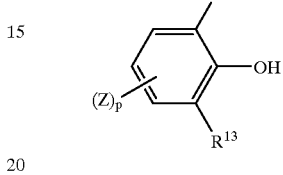

(VIII)

(wherein p stands for a whole number of 0 to 3; $R^{12}$ and $R^{13}$ stand each separately for a substitutional group; and z stands for hydrogen or another substitutional group.)

It is preferable that $R^{12}$ and $R^{11}$ are alkyl group having 1 to 30 carbon atoms or the aryl group having 1 to 30 carbon atoms, and Z is hydrogen, halogen, alkyl group or aryl group.

The substitutional group in the general formula (VIII) may be the same group as an example of the substitutional group X in the aforementioned general formula (II).

Specific examples of the compound of the general formula (VIII) include, but are not limited to, the following:

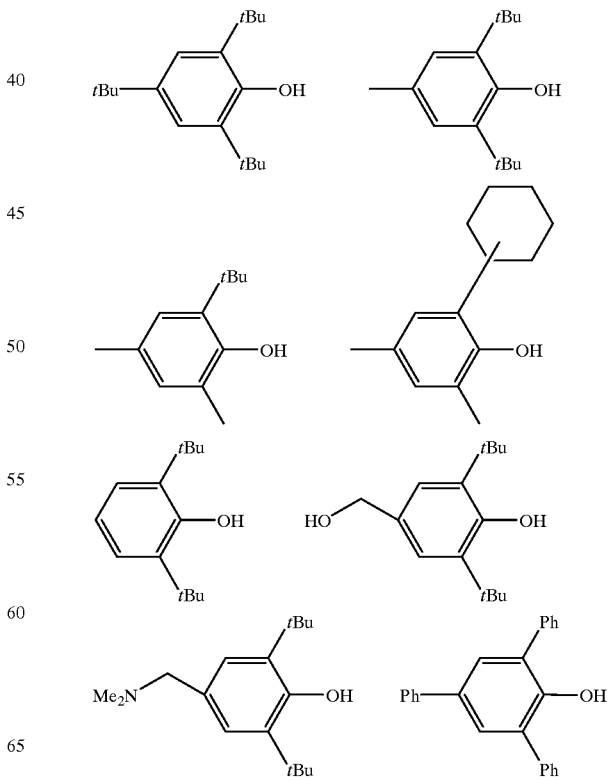

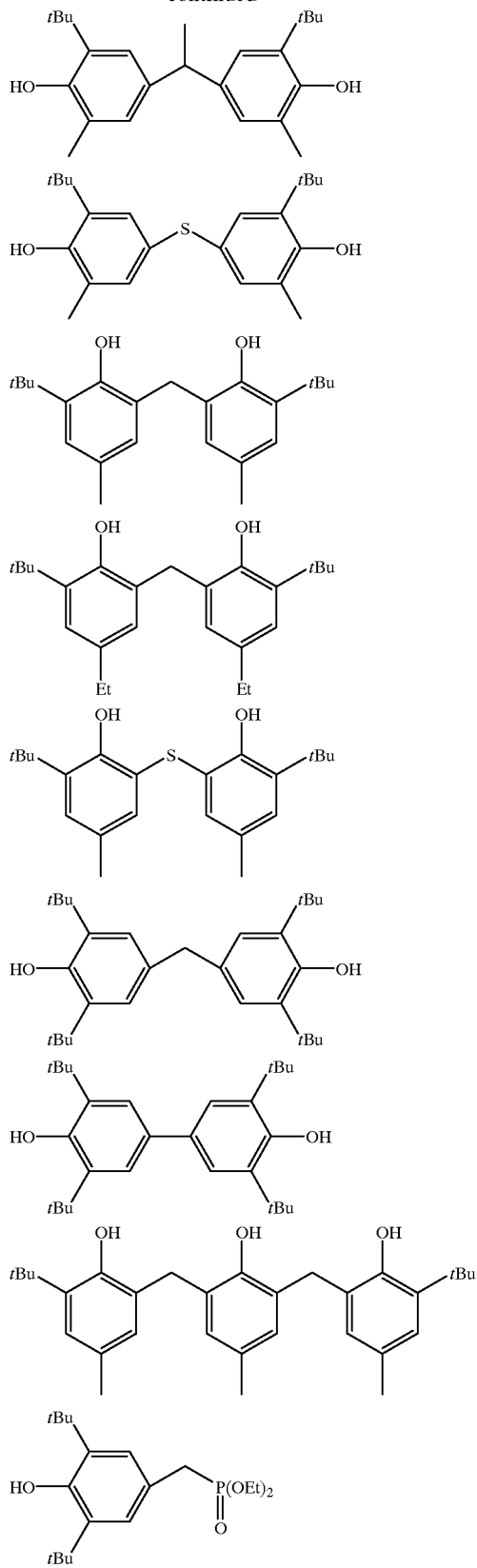

tion include the compounds of the general formula (IX) The compounds of the general formula (IX)

(wherein $R^{14}$, $R^{15}$ and $R^{16}$ stand each separately for hydrogen or another substitutional group.)

It is preferable desirable that R14, R15 and R16 are the alkyl group or the aryl group.

The substitutional group in the general formula (IX) may be the same group as cited as an example of the substitutional group X in the aforementioned general formula (II).

Specific examples of the compound of the general formula (IX) include, but are not limited to, the following:

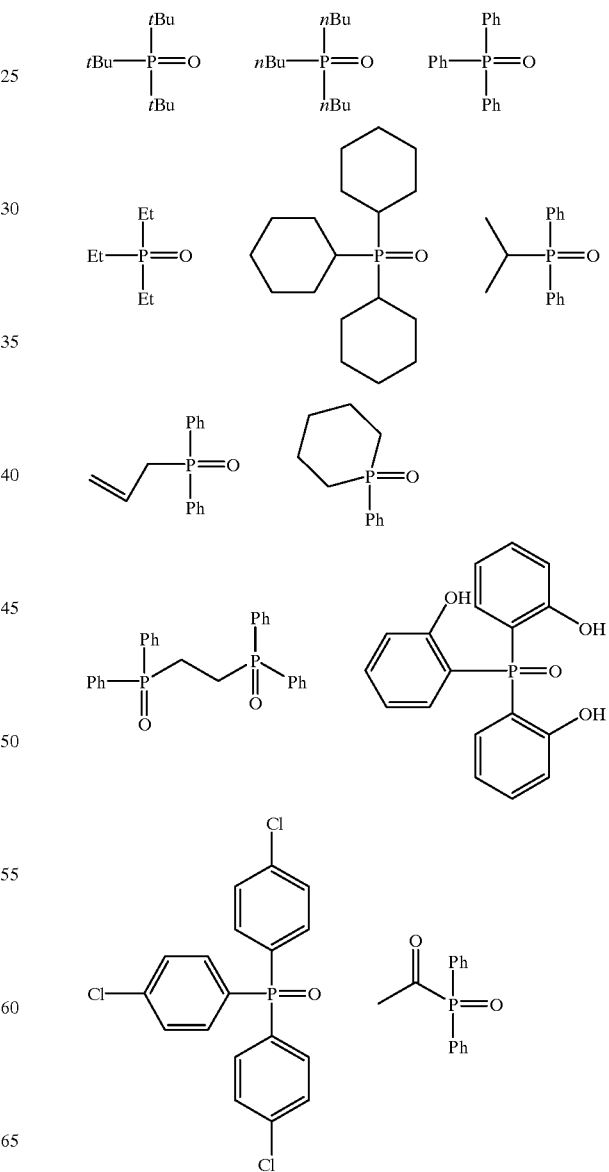

As the compound that can capture radicals, phosphine oxides may be cited. Phosphine oxides of the present inven

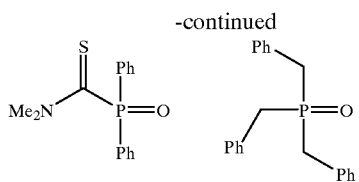

Furthermore, in the process for preparation of the present invention, either phosphineoxide which is stable at room temperature or a compound which turns into phosphineoxide under reaction conditions may be used.

As the compound that turns into phosphineoxide under reaction conditions, the compound represented by the general formula (X) may be cited.

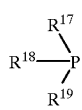

(X)

(wherein $R^{17}$, $R^{18}$ and $R^{19}$ stand each separately for hydrogen or another substitutional group.)

The substitutional group in the general formula (X) may be the same group as an example of the substitutional group X in the aforementioned general formula (II). It is preferable that these substitutional groups are the alkyl group or the aryl group.

Specific examples of the compound of the general formula (X) include, but are not limited to, triphenylphosphine and tributylphosphine.

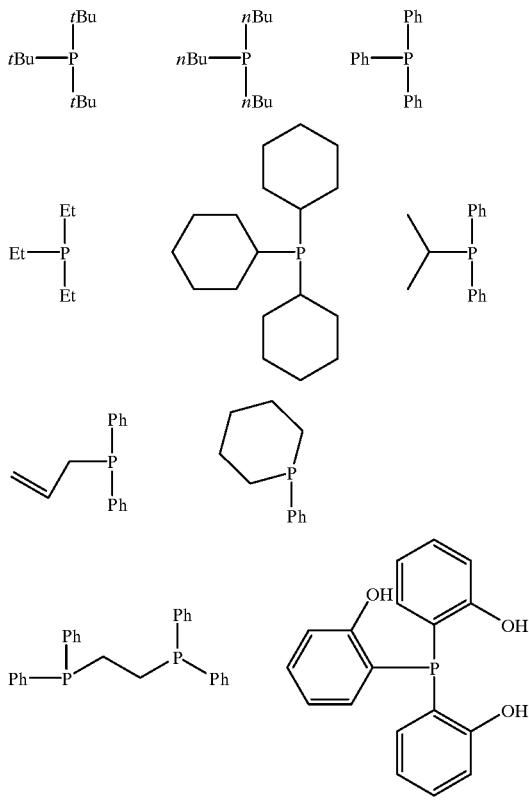

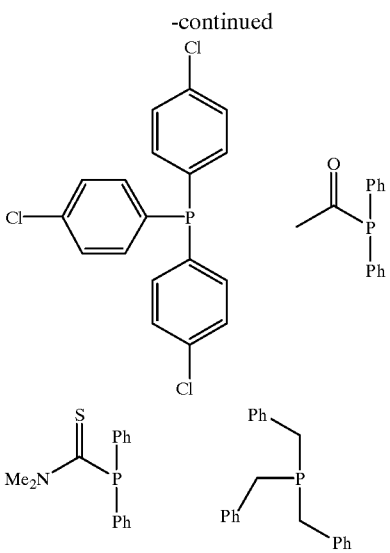

A spin trap agent may be used as the compound that can capture radicals. The spin trap agent is a compound which is used for identifying a radical with a short life that cannot be observed directly by means of ESR, and forms a spin trap compound radical observable with the ESR with the radical to enables to identify the original radical with short life time by ESR analysis.

Specific examples of the compound include, but are not limited to, nitron and nitroso compound as shown below.

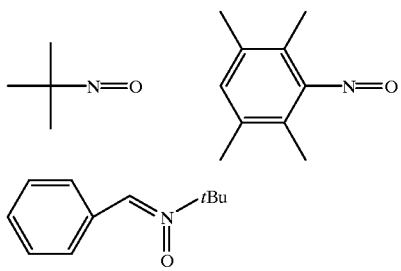

In this invention, the oxidation of hydrocarbon is conducted in the presence of at least one compound that can capture radicals. Two or more compounds that can capture radicals can be used.

Supposing the compound that can capture radicals has captured a radical, the enthalpy (ΔH) to break the bond between the compound and the radical can be determined by calculation by the method as described below. The appropriate range of ΔH depends on the type of the radical to be captured, and the value may be used to select the compound that can capture radicals of the present invention.

Satisfactory results can be obtained by selecting as the compound of the present invention that can capture radicals such compound that the value of enthalpy (ΔH) is −30 to 50 KJ/mon when calculated on the basis of the assumption that the radical to be captured is the radical corresponding to the hydrocarbon to be oxidized (formula I-2). The value of the enthalpy (ΔH) is preferably −25 to 50 KJ/mon, more preferably −20 to 50 KJ/mon. Using the compound that can capture those radicals whose ΔH is within such appropriate range produces satisfactory results as intended by the present invention.

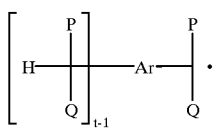

H (heat of formation) calculation method:

H was calculated by conducting structural optimization for the structure showing the smallest amount of energy (most stable structure) by semiempirical molecular orbital method( AM1 method: MOPAC program) after carrying out conformation search by the molecular force field method (CHARMm force field: QUANTA program).

The selection of the compound that can capture radicals has the figures within the appropriate range of $\Delta\epsilon$(SOMO) aforementioned and the value of the enthalpy($\Delta H$) is most preferable in this invention.

Next, given below is an explanation of the reaction conditions of the present invention.

The usage of the compound that can capture radicals or the compound that turns into the compound that can capture radicals in the reaction system in the present invention is normally in the range of 0.00001 to 5.0 parts by weight, preferably in the range of 0.0001 to 0.1 parts by weight, per 100 parts by weight of the starting material hydrocarbon.

As the oxygen-containing gas as the oxidizing agent, air is normally used, but oxygen or any mixed gas of oxygen and nitrogen may also be used.

The reaction may normally be conducted at atmospheric pressure, but it may also be conducted under elevated pressure. The reaction temperature is normally in the range of 40 to 120° C., preferably in the range of 50 to 100° C.

Furthermore, this reaction may be conducted in the presence of a basic compound in the state of a solid or an aqueous solution. Examples of the basic compounds include sodium carbonate, sodium hydrogencarbonate, sodium hydroxide, potassium carbonate, potassium hydrogencarbonate, potassium hydroxide, barium oxide and magnesium oxide. The amount of the basic compound used in the reaction is normally 0.0001 to 10.0 parts by weight, preferably 0.001 to 5.0 parts by weight, per 100 parts by weight of the starting material hydrocarbon.

The reaction in the present invention may be conducted by either batch or continuous method. In the case of conducting the reaction by the batch method, if the starting material hydrocarbon is a liquid at the reaction temperature, the aforementioned compound that can capture radicals or the aforementioned compound that turns into the compound that can capture radicals in the reaction system is added to the starting material and normally made to undergo oxidation reaction by blowing air into the material with heating and agitation. If required, an inactive organic solvent may be used as the reaction solvent in the reaction. On the other hand, if the starting material arylalkyl hydrocarbon is a solid at the reaction temperature, it is made to be dissolved in an inactive organic solvent to form a solution, and the aforementioned compound that can capture radicals or the aforementioned compound that turns into the compound that can capture radicals in the reaction system may be added to the solution and made to undergo oxidation reaction by blowing air into the material with heating and agitation.

Further, in the present invention, a small amount of hydroperoxide which corresponds to the hydrocarbon may be present, as required, as the initiator in the hydrocarbon at the time of the start of the reaction.

A catalyst such as a transition metal complex may also be used additionally as required.

Such catalyst may be formed as a fixed bed, and the starting material hydrocarbon or its solution and air may be caused to pass through the fixed bed, while being mixed.

According to the method of the present invention, the formed hydroperoxide can be easily recovered from the reaction mixture by distillation or any other conventional means after the completion of the reaction and after filtering out the catalyst as required.

EXAMPLES

Given below is a specific description of examples of preparing organic hydroperoxides from arylalkyl hydrocarbon. However, the present invention is not limited in any way by the following examples:

Example 1

18 mg of 2,2,6,6-tetramethylpiperidinoxy were added to a mixture of 144 g of cumene and 36 g of cumenehydroperoxide, and all of them were dissolved. 90 g of 0.05 wt % sodium carbonate were added to it, and this mixture was heated under 6 K pressure to 105° C. Then air was blown into it at a rate of 400 ml/min with vigorous agitation for 3 hours to oxidize cumene.

The rate of accumulation of cumenehydroperoxide during 3 hours from the start of the reaction was determined by iodometry and gas chromatography to be 5.0 wt %/hr. Furthermore, the selectivity of the cumenehydroperoxide which was formed in the reaction was determined by high performance liquid chromatography to be 91 mol %.

The $\Delta\epsilon$ and enthalpy ($\Delta H$) of the 2,2,6,6-tetramethylpiperidinoxy used and the cumyl radicals corresponding to cumene were calculated to be 0.2 eV and −6.4 KJ/mol, respectively.

Example 2

The reaction was conducted in the same manner as Example 1 except that di-t-butylnitroxide was used in place of 2,2,6,6-tetramethylpiperidinoxy.

The rate of accumulation of cumenehydroperoxide during 3 hours from the start of the reaction was determined by iodometry and gas chromatography to be 5.2 wt %/hr. Furthermore, the selectivity of the cumenehydroperoxide which was formed in the reaction was determined by high performance liquid chromatography to be 90 mol %.

The enthalpy ($\Delta H$) of the di-t-butylnitrooxide used and the cumyl radicals corresponding to cumene were calculated to be −15.0 KJ/mol.

Example 3

The reaction was conducted in the same manner as Example 1 except that N-hydroxyphthalimide was used in place of 2,2,6,6-tetramethylpiperidinoxy.

The rate of accumulation of hydroperoxide during 3 hours from the start of the reaction was determined by iodometry and gas chromatography to be 5.0 wt %/hr. Furthermore, the selectivity of the cumenehydroperoxide which was formed in the reaction was determined by high performance liquid chromatography to be 87 mol %.

Example 4

The reaction was conducted in the same manner as Example 1 except that potassium nitrosodisulfonate was used in place of 2,2,6,6-tetramethylpiperidinoxy.

The rate of accumulation of cumenehydroperoxide during 3 hours from the start of the reaction was determined by iodometry and gas chromatography to be 5.1 wt %/hr. Furthermore, the selectivity of the cumenehydroperoxide which was formed in the reaction was determined by high performance liquid chromatography to be 89 mol %.

Example 5

50 mg of 2,2,6,6-tetramethyl-4-piperidinol were added to a mixture of 126 g of cumene and 54 g of cumenehydroperoxide, and all of them were dissolved. 5.6 g of purified water were added to it, and this mixture was heated under 6 K pressure to 105° C. The cumene was oxidized by continuous reaction at a residence time of 1 hour while blowing air into it at a rate of 400 ml/min with vigorous agitation.

The rate of accumulation of cumenehydroperoxide after 4, 5 and 6 hours from the start of the reaction was determined and averaged by iodometry and gas chromatography to be 3.7 wt %/hr. Furthermore, the selectivity of the cumenehydroperoxide which was formed in the reaction was determined and averaged by high performance liquid chromatography to be 92 mol %.

Example 6

The reaction was conducted in the same manner as Example 5 except that 36 mg of bis-(2,2,6,6-tetramethyl-4-piperidinyl)-sebacate was added in place of 2,2,6,6-tetramethyl-4-piperidinol.

The rate of accumulation of cumenehydroperoxide after 4, 5, and 6 hours from the start of the reaction was determined and averaged by iodometry and gas chromatography to be 3.8 wt %/hr. Furthermore, the selectivity of the cumenehydroperoxide which was formed in the reaction was determined and averaged by high performance liquid chromatography to be 90 mol %.

Example 7

5 g of pure water and 36 mg of 2, 4, 6-triphenylphenol were added to a mixture of 122 g of cumene and 53 g of cumenehydroperoxide, and all of them were dissolved as an oil phase. This mixture was heated under 6 K pressure to 105° C. The cumene was oxidized while blowing air into it at a rate of 180 ml/min with vigorous agitation.

A solution of 36 mg of 2,4,6-triphenylphenol dissolved in a mixture of 122 g of cumene and 53 g of cumenehydroperoxide, and pure water were added into the reactor at rates of 175 g/hour and 5 g/hour, respectively, in such manner that the residence time is 1 hour of continuous reaction. The reaction liquid was collected by overflow into another vessel three times every hour after 4 hours from the start of the reaction.

The rate of accumulation of cumenehydroperoxide was determined by iodometry and gas chromatography. The average of three determination values was 3.8 wt %/hr. Furthermore, the selectivity of the cumenehydroperoxide which was formed in the reaction was determined by high performance liquid chromatography. The average of three determination values was 89 mol %.

The $\Delta\epsilon$(SOMO) and enthalpy ($\Delta H$) between the 2,4,6-triphenylphenoxy radical presumed to be formed from the 2,4,6-triphenylphenol used and cumyl radical corresponding to cumene were calculated to be 0.4 eV and 16.5 KJ/mon, respectively.

Example 8

The reaction was conducted in the same manner as Example 7 except that 2,6-di-t-butyl-4-methylphenol was added in place of 2,4,6-triphenylphenol.

The rate of accumulation of cumenehydroperoxide was determined by iodometry and gas chromatography. The average of three determination values was 3.5 wt %/hr. Furthermore, the selectivity of the cumenehydroperoxide which was formed in the reaction was determined by high performance liquid chromatography to be 90 mol %.

Example 9

5 g of pure water and 36 mg of triphenylphosphineoxide were added to a mixture of 122 g of cumene and 53 g of cumenehydroperoxide, and all of them were dissolved as an oil phase. This mixture was heated under 6 K pressure to 105° C. Then air was blown into it at a rate of 180 ml/min with vigorous agitation to oxidize cumene.

A solution of 36 mg of triphenylphosphineoxide dissolved in a mixture of 122 g of cumene and 53 g of cumenehydroperoxide and pure water were added to the reactor at rates of 175 g/hour and 5 g/hour, respectively, in such manner that the residence time is 1 hour of continuous reaction. The reaction liquid was collected by overflow into another vessel three times every hour after 4 hours from the start of the reaction.

The rate of accumulation of cumenehydroperoxide was determined by iodometry and gas chromatography. The average of three determination values was 4.5 wt %/hr. Furthermore, the selectivity of the cumenehydroperoxide which was formed in the reaction was determined by high performance liquid chromatography. The average of three determination values was 90 mol %.

Example 10

The reaction was conducted in the same manner as described in Example 9 except that tri-t-butylphosphineoxide was used as an additive in place of triphenylphosphineoxide.

The rate of accumulation of cumenehydroperoxide was determined by iodometry and gas chromatography. The average of three determination values was 3.5 wt %/hr. Furthermore, the selectivity of the cumenehydroperoxide which was formed in the reaction was determined by high performance liquid chromatography to be 90 mol %.

Comparative Example 1

The reaction was conducted in the same manner as Example 1 except that 2,2,6,6-tetramethylpiperidinoxy was not used.

The rate of accumulation of cumenehydroperoxide during 3 hours from the start of the reaction was determined by iodometry and gas chromatography to be 5.5 wt %/hr. Furthermore, the selectivity of the cumenehydroperoxide which was formed in the reaction was determined by high performance liquid chromatography to be 84 mol %.

Comparative Example 2

The reaction was conducted in the same manner as Comparative Example 1 except that the reaction temperature was set at 100° C.

The rate of accumulation of cumenehydroperoxide during 3 hours from the start of the reaction was determined by iodometry and gas chromatography to be 4.1 wt %/hr. Furthermore, the selectivity of the cumenehydroperoxide which was formed in the reaction was determined by high performance liquid chromatography to be 88 mol %.

Comparative Example 3

The reaction was conducted in the same manner as Example 5 except that 2,2,6,6-tetramethyl-4-piperidinol was not used.

The rate of accumulation of cumenehydroperoxide during 3 hours from the start of the reaction was determined and averaged by iodometry and gas chromatography to be 5.5 wt %/hr. Furthermore, the selectivity of the cumenehydroperoxide which was formed in the reaction was determined and averaged by high performance liquid chromatography to be 86 mol %.

Comparative Example 4

The reaction was conducted in the same manner as Comparative Example 3 except that the reaction temperature was set at 100° C.

The rate of accumulation of cumenehydroperoxide during 4, 5 and 6 hours from the start of the reaction was determined and averaged by iodometry and gas chromatography to be 3.9 wt %/hr. Furthermore, the selectivity of the cumenehydroperoxide which was formed in the reaction was determined and averaged by high performance liquid chromatography to be 89 mol %.

Comparative Example 5

The reaction was conducted in the same manner as Example 7 except that 2,4,6-triphenylphenol was not used.

The rate of accumulation of cumenehydroperoxide was determined by iodometry and gas chromatography. The average of three determination values was 5.5 wt %/hr. Furthermore, the selectivity of the cumenehydroperoxide which was formed in the reaction was determined by high performance liquid chromatography to be 86 mol %.

Comparative Example 6

The reaction was conducted in the same manner as Comparative Example 5 except that the reaction temperature was set at 100° C.

The rate of accumulation of cumenehydroperoxide was determined by iodometry and gas chromatography. The average of three determination values was 3.9 wt %/hr. Furthermore, the selectivity of the cumenehydroperoxide which was formed in the reaction was determined by high performance liquid chromatography to be 88 mol %.

What we claim is:

1. A process for preparing arylalkyl hydroperoxides, comprising:

oxidizing an arylalkyl hydrocarbon represented by the following formula (I):

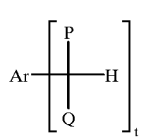
(I)

wherein P and Q may be the same or different from each other and represent hydrogen or an alkyl group, t represents a whole number of 1 to 3, and Ar represents an aromatic hydrocarbon group;

with an oxygen-containing gas in the presence of a compound represented by formula (III), or a compound that forms the compound represented by formula (III) in the reaction system:

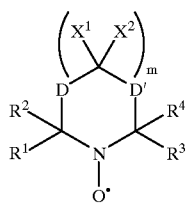
(III)

wherein m represents a whole number of 0 to 3, D and D' each separately represents:

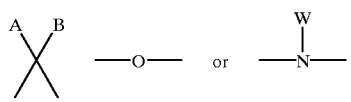

and wherein A, B, $X^1$, $X^2$, $R^1$, $R^2$, $R^3$, $R^4$ and W each separately represents hydrogen or a substituent comprising an element selected from the group consisting of hydrogen, carbon, oxygen, nitrogen, sulfur, phosphorus, silicon and halogen; and wherein each carbon atom ring member or each nitrogen atom ring member may form a double bond between adjoining atoms.

2. The process according to claim 1, wherein the arylalkyl hydrocarbon of formula (I) is cumene, cymene, m-diisopropylbenzene, p-diisopropylbenzene, 1,3,5-triisopropylbenzene, isopropylnaphthalene, diisopropylnaphthalene, isopropylbiphenyl, diisopropylbiphenyl or a mixture of two or more thereof.

3. The process according to claim 2, wherein the arylalkyl hydrocarbon is cumene.

4. The process according to claim 1, wherein the compound of formula (III) is a compound having a structure in which two or more structures of formula (III) are crosslinked through any of the groups selected from $X^1$, $X^2$, A and B.

5. The process according to claim 1, wherein A, B, $X^1$, $X^2$, $R^1$, $R^2$, $R^3$, $R^4$ and W each separately represents hydrogen or a substituent selected from the group consisting of alkyl, aryl, halogen, cyano, amino, isothiocyanic acid, —COOR$_a$ (wherein R$_a$ represents hydrogen, an alkyl group or an aryl group), (di)alkylaminoalkyl, hydroxyl, hydroxyalkyl, alkoxy, arylalkoxy, —CONR$_b$R$_c$ (wherein R$_b$ and R$_c$ each separately represents hydrogen, an alkyl group or an aryl group), maleimide, and phosphoric acid; or A and B together, $X^1$ and $X^2$ together, $R^1$ and $R^2$ together or $R^3$ and $R^4$ together may independently form an oxo group (═O) or a (═NH) group.

6. The process according to claim 1, wherein $R^1$, $R^2$, $R^3$, $R^4$ represent an alkyl group.

7. The process according to claim 6, wherein the compound represented by formula (III) is 2,2,6,6-tetraalkyl piperidinooxy radical, 4-hydroxy-2,2,6,6-tetraalkyl piperidinyloxy radical, bis-(2,2,6,6-tetraalkyl piperidinoxyl)-sebacate radical or 2,2,5,5-tetraalkyl pyrrolydinoxy radical.

8. The process according to claim 1, wherein a SOMO (single occupied molecular orbital) energy level of the compound represented by formula (III) and a SOMO energy level of a radical corresponding to said arylalkyl hydrocarbon which is represented by formula (I-2) are calculated by the MNDO-PM3 method, and wherein the difference (Δ(SOMO)) of the SOMO energy levels is used to select a compound represented by formula (III);

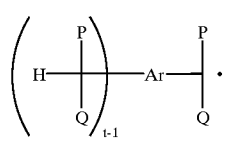

(I-2)

wherein P and Q may be the same or different from each other and represent hydrogen or an alkyl group, t represents a whole number 1 to 3, and Ar represents an aromatic hydrocarbon group.

9. The process according to claim 8, wherein the difference ($\Delta\epsilon$(SOMO)) of the SOMO energy levels is not more than 10 eV.

10. The process according to claim 9, wherein the difference ($\Delta\epsilon$(SOMO)) of the SOMO energy levels is not less than 0 eV and not more than 10 eV.

11. The process according to claim 8, 9 or 10, wherein a calculated enthalpy ($\Delta H$) value to break a theoretical bond between the compound represented by formula (III) and the radical represented by formula (I-2) is −30 to 50 KJ/mol.

12. A process for preparing arylalkyl hydroperoxides, comprising:

oxidizing an arylalkyl hydrocarbon represented by formula (I) with an oxygen-containing gas in the presence of at least one nitroxide radical or a compound that forms a nitroxide radical in the reaction system:

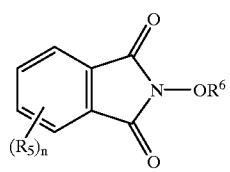

(I)

wherein P and Q may be the same or different from each other and each represents hydrogen or an alkyl group, t represents a whole number of 1 to 3, and Ar represents an aromatic hydrocarbon group, wherein the compound that forms a nitroxide radical is at least one compound selected from the group consisting of formula (V), formula (VI) and formula (VII):

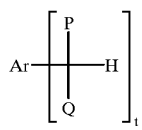

(V)

wherein n represents a whole number of 0 to 4, and $R^5$ and $R^6$ each separately represents hydrogen or a substituent comprising an element selected from the group consisting of hydrogen, carbon, oxygen, nitrogen, sulfur, phosphorus, silicon and halogen;

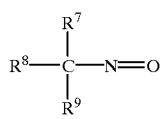

(VI)

wherein $R^7$, $R^8$ and $R^9$ each separately represents hydrogen or a substituent comprising an element selected from the group

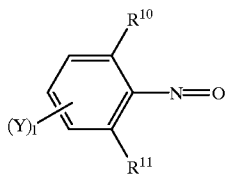

consisting of hydrogen, carbon, oxygen, nitrogen, sulfur, phosphorus, silicon and halogen;

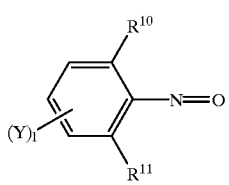

(VII)

wherein I represents a whole number of 0 to 3; and Y, $R^{10}$ and $R^{11}$ each separately represents hydrogen or a substituent comprising an element selected from the group consisting of hydrogen, carbon, oxygen, nitrogen, sulfur, phosphorus, silicon and halogen.

13. The process according to claim 12, wherein the arylalkyl hydrocarbon is cumene.

14. A process for preparing arylalkyl hydroperoxides, comprising:

oxidizing an arylalkyl hydrocarbon represented by the following formula (I):

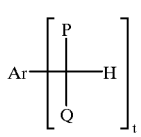

(I)

wherein P and Q may be the same or different from each other and represent hydrogen or an alkyl group, t represents a whole number of 1 to 3, and Ar represents an aromatic hydrocarbon group;

with an oxygen-containing gas in the presence of a compound represented by formula (II), or a compound that forms the compound represented by formula (II) in the reaction system;

$(X)_n$—Z—O. (II)

wherein Z represents sulfur or phosphorus, X is the same or different from one another and is a substituent selected from the group consisting of hydrogen atom, halogen atom, hydrocarbon group, heterocyclic compound, oxygen-containing group, nitrogen-containing group, boron-containing group, sulfur-containing group, phosphorus-containing group, and silicon-containing group or X is a ring formed by not less than two of said substituents connected to each other, wherein the substituent X is optionally substituted and n represents a w hole number of 1 to 4; and said oxidizing step is performed in the absence of a transition metal complex catalyst.

15. The process according to claim 14, wherein X is the same or different from one another and is a substituent selected from the group consisting of a straight-chain or branched alkyl group having 1 to 30 carbon atoms, a straight-chain or branched alkenyl group having 2 to 30 carbon atoms, a straight-chain or branched alkynyl group having 2 to 30 carbon atoms, a cyclic saturated hydrocarbon groups having 3 to 30 carbon atoms, a cyclic unsaturated hydrocarbon group having 5 to 30 carbon atoms and an aryl group having 6 to 30 carbon atoms, wherein the substituent X is optionally substituted.

16. The process according to claim 14, wherein the hydrocarbon group is selected from the group consisting of benzyl, cumyl, tolyl, isopropylphenyl, t-butylphenyl, dimethylphenyl and di-t-butylphenyl; the heterocyclic compound is selected from the group consisting of pyrrole, pyridine, pyrimidine, quinoline, triazine, furan, pyran, and thiophene, and wherein the heterocyclic compound is optionally substituted with a $C_{1-30}$ alkyl or a $C_{1-30}$ alkoxy group; the oxygen-containing group is selected from the group consisting of alkoxy, aryloxy, ester, acyl, carboxyl, carbonate, hydroxy, peroxy, and carboxylic acid anhydride; the nitrogen-containing group is selected from the group consisting of amino group, imino group, amide group, imide group, hydrazino group, hydrazono group, nitro group, nitroso group, cyano group, isocyano group, ester cyanate group, amidino group, diazo group and ammonium salt; the boron-containing group is selected from the group consisting of boranediyl, boranetolyl, and diboranyl; the sulfur-containing group is selected from the group consisting of mercapto group, thioester group, dithioester group, alkylthio group, arylthio group thioacyl group, thioether group, thiocyanate group, isocyanate group, sulfonester group, sulfonamide group, thiocarboxyl group, dithiocarboxyl group, sulfo group, sulfonyl group, sulfinyl group and sulphenyl group; the phosphorus-containing group is selected from the group consisting of phosphide, phosphoryl, thiophosphoryl and phosphato; and the silicon-containing group is selected from the group consisting of methyl silyl, dimethylsilyl, trimethylsilyl, ethylsilyl, diethylsilyl, triethyisilyl, diphenylmethylsilyl, triphenylsilyl, dimethyiphenysilyl, dimethyl-t-butylsilyl, and dimethyl(pentafluorophenyl)silyl.

17. The process according to claim 1, wherein the substituent comprising carbon is selected from the group consisting of benzyl, cumyl, tolyl, isopropyephenyl, t-butylphenyl, dimethylphenyl and di-t-butylphenyl; the substituent comprising oxygen is selected from the group consisting of alkoxy, aryloxy, ester, acyl, carboxyl, carbonate, hydroxy, peroxy, and carboxylic acid anhydride; the substituent comprising nitrogen is selected from the group consisting of amino group, imino group, amide group, imide group, hydrazino group, hydrazono group, nitro group, nitroso group, cyano group, isocyano group, ester cyanate group, amidino group, diazo group and ammonium salt; the substituent comprising sulfur is selected from the group consisting of mercapto group, thioester group, dithioester group, alkylthio group, arylthio group, thioacyl group, thioether group, thiocyanate group, isocyanate group, sulfonester group, sulfonamide group, thiocarboxyl group, dithiocarboxyl group, sulfo group, sulfonyl group, sulfinyl group and sulphenyl group; the substituent comprising phosphorus is selected from the group consisting of phosphide, phosphoryl, thiophosphoryl and phosphato; and the substituent comprising silicon is selected from the group consisting of methyl silyl, dimethylsilyl, trimethylsilyl, ethylsilyl, diethylsilyl, triethylsilyl, diphenylmethylsilyl, triphenylsilyl, dimethylphenylsilyl, dimethyl-t-butylsilyl, and dimethy(pentafluorophenyl)silyl.

18. The process according to claim 14, wherein the arylalkyl hydrocarbon of formula (I) is cumene, cymene, m-diisopropylbenzene, p-diisopropylbenzene, 1,3,5-triisopropylbenzene, isopropylnaphthalene, diisopropylnaphthalene, isopropylbiphenyl, diisopropylbiphenyl or a mixture of two or more thereof.

19. The process according to claim 18, wherein the arylalkyl hydrocarbon is cumene.

20. The process according to claim 14, wherein a SOMO (single occupied molecular orbital) energy level of the compound represented by formula (II) and a SOMO energy level of a radical corresponding to said arylalkyl hydrocarbon which is represented by formula (I-2) are calculated by the MNDO-PM3 method, and wherein the difference ($\Delta\epsilon$ (SOMO)) of the SOMO energy levels is used to select a compound represented by formula (II),

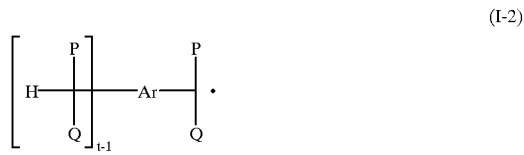

(I-2)

wherein P and Q may be the same or different from each other and represent hydrogen or an alkyl group, t represents a whole number of 1 to 3, and Ar represents an aromatic hydrocarbon group.

21. The process according to claim 20, wherein the difference ($\Delta\epsilon$(SOMO)) of the SOMO energy levels is not more than 10 eV.

22. The process according to claim 21, wherein the difference ($\Delta\epsilon$(SOMO)) of the SOMO energy levels is not less than 0 eV and not more than 10 eV.

23. The process according to claims 20, 21 or 22, wherein a calculated enthalpy ($\Delta H$) value to break a theoretical bond between the compound represented by formula (II) and the radical represented by formula (I-2) is −30 to 50 KJ/mol.

24. A process for preparing arylalkyl hydroperoxides, comprising:
oxidizing an arylalkyl hydrocarbon represented by the following formula (I):

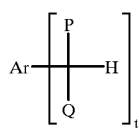
(I)
wherein P and Q may be the same or different from each other and represent hydrogen or an alkyl group, t represents a whole number of 1 to 3, and Ar represents an aromatic hydrocarbon group;
with an oxygen-containing gas in the presence of at least one nitroxide radical selected from the group consisting of (1) to (8):
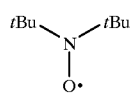
(1)
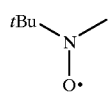
(2)
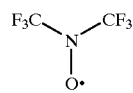
(3)
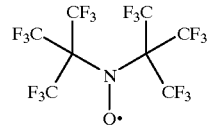
(4)
(5)
(6)
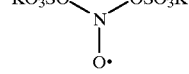
(7)
(8)
* * * * *